A. PERRY
ROSE PLANT
Filed March 28, 1974
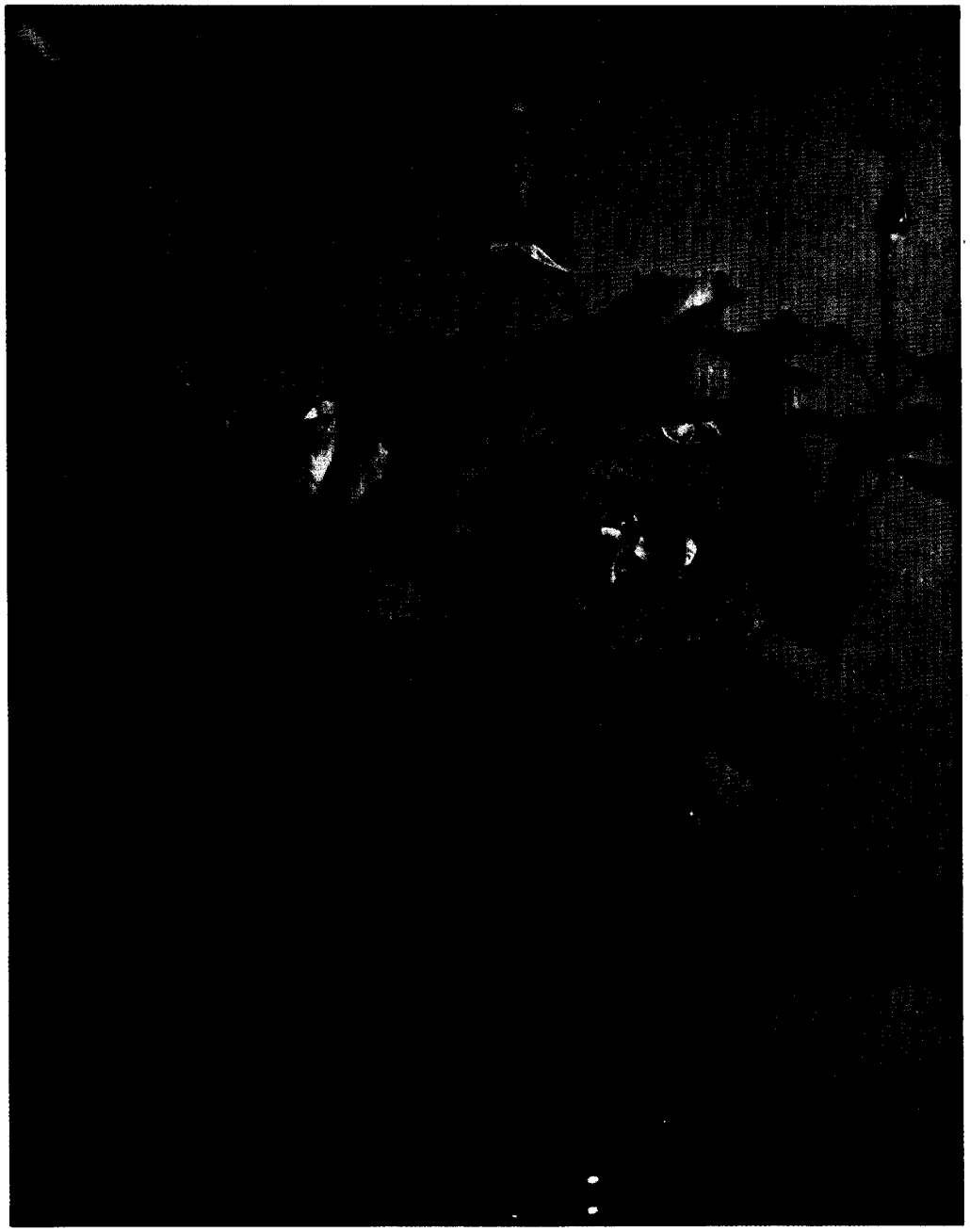

United States Patent

Plant Pat. 3,788
Patented Sept. 23, 1975

3,788
ROSE PLANT

Anthony Perry, Garden Grove, Calif., assignor to Henry A. Conklin, McFarland, Calif.

Filed Mar. 28, 1973, Ser. No. 345,694
Int. Cl. A01h 5/00
U.S. Cl. Plt.—20 1 Claim The present invention relates to a new and distinct variety of rose plant of the hybrid tea class, which was originated by me by crossing the variety "Queen Elizabeth" (Plant Pat. No. 1,259) with the variety "Helen Traubel" (Plant Pat. No. 1,028).

As the result of this breeding, I have produced a new and improved rose variety having the following unique combination of characteristics which are outstanding therein and which distinguish it from its parents, as well as from all other varieties of which I am aware:

(1) Extraordinary vigorous growth which is evidenced by the fact that the new variety is among the strongest growing in the hybrid tea class;

(2) A habit of usually producing only one flower to a stem; however, an occasional bloom will appear with one strong side bud on a 5- to 6-inch stem adding character and variety to the cut flowers when used for bouquet or arrangement purposes, with the flowers being borne on exceptionally long stems growing from the base or near the base of the plant, and the stems being substantially less thorny than those of most red hybrid tea rose varieties;

(3) Exceptionally large flower size, with the flowers measuring 4½ to 5 inches when fully open, which open slowly and last for a long time without loss of color, both when used as a cut flower and when left in the garden;

(4) Good flower petalage normally numbering from 34 to 36 petals, with the petals being large and broad and having very good texture, the first outer petal having a tendency to be slightly shorter than all the rest;

(5)A regular arrangement of the petals in the open flowers, with a high degree of imbrication, fully open flower having tendency to be slightly flatter than that of the seed parent;

(6) A distinctive and attractive general color tonality of the flowers which may be generally described as medium red, but the color being lighter and brighter than the flowers of such varieties as "Chrysler Imperial" or "Mister Lincoln," said flowers also having a white vegetative streak on the inner petals of the flowers; and (7) In comparing with its parents, many of the best features of both "Queen Elizabeth" (seed parent) and "Helen Traubel" (pollen parent) have been achieved in this new variety, the desirable features of which are a vigorous upright growing habit, not as tall as "Queen Elizabeth" but stronger and better branched than "Helen Traubel," a larger bloom than that of "Queen Elizabeth" with more petals than the bloom of "Helen Traubel," smooth long cutting stems almost thornless, similar to "Helen Traubel" but much stiffer and longer than the short clustered stems of "Queen Elizabeth," dark green disease-resistant foliage, a feature derived from both parents and a pleasant fragrance transmitted from the pollen parent, "Helen Traubel," the dominance of the red color genes in both parents' lineage is reflected in the bright medium red flower of this new seedling.

Flower production is outstanding throughout the growing season with better flower products than most of the larger hybrid teas during the hot dry growing periods. Under a cool climate and late fall growing conditions the bright medium red flower takes on a deeper scarlet tone in the open bud, adding to the beauty of the flower.

Asexual reproduction of my new variety by budding, as performed at McFarland, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Nickerson Color Fan, published by Munsell Color Company, Incorporated, of Baltimore, Md. and Wilson's Horticultural Colour Chart (1940), except where general color terms of ordinary dictionary significance are obvious:

Type: Hardy; tall; bush; outdoor; seedling; for cut flowers and for garden decoration.
Class: Hybrid tea.
Breeding: Seedling.
*Seed parent.*—"Queen Elizabeth."
*Pollen parent.*—"Helen Traubel."
Propagation: Holds its distinguishing characteristics through succeeding propagations by budding.

FLOWER

Locality where grown and observed: McFarland, Calif.
Flowers borne: Usually singly and rarely more to stem and then only with single side bud.
Quantity of bloom: From moderate to free, outdoors.
Continuity: More or less continuous during growing season.
Fragrance: Strong. Nature—a mixture of damask and tea.
Bud:
*Peduncle.*—Long; heavy; erect; stiff; almost smooth; with few stipitate glands. Color—medium green.
*Before calyx breaks.*—Size—medium for class. Form—long; pointed; with foliaceous appendages on the surface of the bud; often with foliaceous parts extending beyond the tip of the bud equal to ¾ or more of its length. Color—Dark Red, Plate 2.5R 3/7.
*As calyx breaks.*—Color—Dark Red, Plate 2.5R 3/7.
*As first petal opens.*—Size—large. Form—more or less urn-shaped. Color: outside—between Moderate Red, Plate 2.5R 4/10 and Deep Purplish Red, Plate 10RP 3/10; inside—between Strong Red, Plate 2.5R 5/12 and Moderate Red, Plate 2.5R 4/10, but brighter due to an undertone of yellow and a velvety nap.
*Opening.*—Opens up well.
Bloom:
*Size (when fully open).*—Large; from 4½ inches to 5 inches or more.
*Petalage.*—From double to very double; from 34 to 36 petals plus 4 to 6 petaloids; arranged regularly.
*Form.*—From cupped to high-centered at first, but becoming from flat cupped; petals at first being loosely rolled outward and remaining loosely rolled outward at maturity.
Petals:
*Texture.*—Thick; leathery.
*Appearance.*—Inside—velvety. Outside—from shiny to satiny.
*Shape.*—Outside—very broadly orbicular, with apex having 1 or 2 notches, and often with one or two notches on lower portion of either or each lateral margin. Intermediate—from broadly obovate to broadly orbicular, with apex acute, and having 1 or 2 notches. Inside—from obovate to orbicular, with apex acute and having 1 notch or being entire.

This description of a newly opened flower was made from a rose grown outdoors during the month of November at McFarland, Calif.:

*Color.*—The upper and lower petal surfaces are slightly darker than Cherry 722, with the color becoming lighter and brighter as the blossoms age, approaching Cherry 722/3. The point of attachment is Yellow, 5Y 8/12. The veins exhibit varying degrees of black, and the inner petals often exhibit white vegetative streaks.

*General color effect.*—Cherry, 722 through 722/3.

*Behavior.*—Drop off cleanly, except for occasional petaloids.

*Flower longevity.*—On bush in garden—5 or 6 days in November. Cut roses grown outdoors and kept at living-room temperatures—4 or 5 days in November.

REPRODUCTIVE ORGANS

Stamens: Medium quantity; arranged more or less irregularly, partly about pistils and partly mixed with petaloids.

Filaments: Medium long; most with anthers. Color—yellow.

Anthers: Small for class; open at various times. Color—yellow.

Pollen: From sparse to moderate quantity. Color—yellow.

Pistils: Medium quantity.

Styles: Uneven; from medium length to long; from thin to medium caliper; arranged very irregularly, being twisted, bent, matted, etc.

Stigma: Color—yellow.

Ovaries: Most enclosed in, but some protruding from calyx.

Hips: Usually very short; flat; globular; sometimes with a conspicuous neck; moderately smooth; walls thick and fleshy. Color—yellow, with some reddish markings and becoming near orange color when mature.

Sepals: Permanent; moderately long; more or less straight and spear-shaped, but sometimes curled.

Seeds: From few to many; medium size for class; usually from 6 to 20 seeds per hip.

PLANT

Foliage:

*Leaves.*—Compound of 3, 5, or 7 leaflets; normal quantity; large size; moderately heavy, leathery; non-glossy.

*Leaflets.*—Shape—elliptic, with apex from acute to acuminate. Base—from round to cuneate. Margin—both simply and doubly serrate.

*Color.*—Mature: upper surface—dark green; under surface—gray-green. Young: upper surface—basically yellowish green, overlaid with dark purplish red, especially on veins; under surface—reddish purple reticulations almost completely dominate basic yellow-green.

*Rachis (the supporting stem of the compound leaf).*—Medium weight. Upper side—grooved; edges lined with stipitate glands. Under side—sparsely prickly.

*Stipules.*—Medium length; mostly adnate to petiole; narrow; with short points turning out at an angle of more than 45°.

*Disease resistance.*—Medium resistance to powdery mildew, as determined by comparison with other red rose varieties grown under comparable conditions at McFarland, Calif.

Growth:

*Habit.*—Tall; bushy; upright; much-branched.

*Growth.*—Very vigorous.

*Canes.*—Heavy.

*Main stems.*—Color—yellow green. Large prickles—several; medium length; straight; with short, broad base; color—gray-brown. Small prickles—several; color—gray-brown. Hairs—few; color—brown.

*Branches.*—Color—gray-green. Large prickles—several; medium length; straight; with short, broad base; color—brown. Small prickles—several; color—brown. Hairs—few; color—brown.

*New shoots.*—Color—purplish red. Large prickles—several; medium length; straight; with short, broad base; color—purplish red. Small prickles—several; color—reddish purple. Hairs—few; color—reddish purple.

I claim:

1. A new and distinct variety of rose plant of the hybrid tea class, substantially as herein shown and described, characterized particularly as to novelty by the unique combination of an extraordinarily vigorous and large habit of growth, a habit of usually bearing flowers singly on long stems, with fewer prickles than the average red hybrid tea rose varieties, exceptionally large flower size, good flower petalage, with the individual petals being very large and broad, regular arrangement of the petals in the open flowers, with a high degree of imbrication, a distinctive and attractive medium red general color tonality of the flowers, said flowers having a white vegetative streak on the midrib of some of the inner petals, and a distinctive and strong flower fragrance characterized by a blend of tea and damask.

No references cited.

ROBERT E. BAGWILL, Primary Examiner